United States Patent [19]
Rossi

[11] Patent Number: 5,695,938
[45] Date of Patent: Dec. 9, 1997

[54] ANTI-HIV RIBOZYMES

[75] Inventor: John J. Rossi, Rancho Cucamonga, Calif.

[73] Assignee: City of Hope, Duarte, Calif.

[21] Appl. No.: 654,773

[22] Filed: May 29, 1996

Related U.S. Application Data

[63] Continuation of Ser. No. 355,244, Dec. 9, 1994, abandoned.

[51] Int. Cl.$^6$ .............................. C12Q 1/68; C12N 15/85
[52] U.S. Cl. ..................... 435/6; 435/91.31; 435/172.1; 435/172.3; 435/320.1; 435/366; 435/372.3; 536/23.1; 536/23.2; 536/24.5
[58] Field of Search ..................... 435/6, 91.31, 320.1, 435/172.3, 172.1, 366, 372.3, 240.1; 536/23.1, 23.2, 24.5; 514/44

[56] References Cited

PUBLICATIONS

Guatell: et al. J. Cell. Biochem. Supple 16E 1992:79 #Q521.
Johnston et al. 260: 1286–1293 (1993), Science.
Barinaga Science 262: 1512–1514 (1993).
Sarver et al. Science 246:1222–1225 (1990).
Miller et al. Biotechniques 7:980–990 (1989).
Ratner et al. Nature 313:277 (1985).
Zhon et al. Gene 149:33–39 (1994).
Rossi et al. Derwent Biotechnology Asbstr. No: 95–00442.
Wong et al. Blood V. 84, No. 10 Nov. 15, 1994 pp. 743a, #2957.

*Primary Examiner*—John L. LeGuyader
*Attorney, Agent, or Firm*—Rothwell, Figg, Ernst & Kurz

[57] ABSTRACT

Ribozymes targeted against two portions of the HIV-1 genome were designed to cleave HIV RNA in the tat gene (TAT) or in a common exon for tat and rev (TR). The ribozymes were cloned into the LN (LTR-neomycin) retroviral vector plasmids and expressed as part of vital LTR-driven transcripts. The vectors were packaged as amphitropic virions and used to transduce human T-lymphocytes. Expression of the vector transcripts containing the ribozyme sequences were readily detected by Northern blot analysis of the transduced T cells. The T-lymphocytes expressing the anti-HIV-1 ribozymes showed resistance to HIV-1 replication.

11 Claims, 5 Drawing Sheets

ANTI-HIV RIBOZYMES

This is a continuation of application Ser. No. 08/355,244, filed Dec. 9, 1994, now abandoned.

This invention was made with government support under Grant No. J. R. NIAID R01 AI29329 awarded by the National Institutes of Health. The government has certain rights in the invention.

FIELD OF THE INVENTION

This invention relates to combinations of ribozymes. More particularly, the invention relates to combinations of two or more ribozymes, each such ribozyme being targeted to a different portion of a viral genome, in particular an HIV-1 or other lentiviral genome.

ABBREVIATIONS

The following abbreviations are used in this application:
A=absorbance (1 cm)
AIDS=acquired immune deficiency syndrome
bp=base pair(s)
CMV=cytomegalovirus
DCT=double-copy tRNA
ELISA=enzyme-linked immunosorbent assay
HIV=human immuno-deficiency virus
IE=immediate early
kb=kilobase(s) or 1000 bp
LN=LTR-Nm
LTR=long terminal repeat
MoMuLV=Moloney murine leukemia virus
Nm=neomycin
nt=nucleotide(s)
rev (Rev)=regulates envelope expression
Rz=ribozyme(s)
tat (Tat)=transactivator of transcription
TR=common exon for tat and rev

BACKGROUND OF THE INVENTION

The concepts of genetic therapies for the treatment of genetic defects or providing intracellular immunity to viral infection have been entertained for a number of years (see Baltimore, 1988 (1); Szybalski, 1992 (2)). Gene therapy has recently received more attention for its potential utility in the treatment of HIV infection (Sarver and Rossi, 1993 (3)). A number of different inhibitory strategies have been tested for conferring resistance to HIV-1, including those encoding antisense RNA, ribozymes (Rz), TAR or RRE decoys, trans-dominant mutant HIV-1 genes and conditionally lethal toxins (reviewed in Sarver and Rossi, 1993 (3)).

RNA-based strategies, such as antisense or Rz, have the dual advantages of being sequence-specific, theoretically eliminating unwanted toxicities, as well as not producing potentially immunogenic proteins. A single Rz molecule is capable of irreversibly inactivating multiple target RNA molecules by sequential cycles of binding, cleavage and release, but even in the absence of multiple substrate turnover, Rz functionally inactivate target RNAs via cleavage (Zaug and Cech, 1986 (4); Uhlenbeck, 1987 (5); Castanotto, et al., 1992 (6)).

Retroviral vectors currently comprise a relatively efficient system for gene transduction of mammalian cells, including human lymphocytes and hematopoietic cells (Mulligan, 1993 (7); Williams, 1990 (8)). Retroviral vectors and packaging cell lines have been developed which have extremely low probabilities of producing replication-competent retroviruses and are increasingly used for clinical gene marking and gene therapy trials (Miller and Rosman, 1989 (9); Miller, 1990 (10); Anderson, et al., 1993 (11)).

SUMMARY OF THE INVENTION

This invention provides two hammerhead Rz which are complementary to the HIV-1 genome, in the tat gene and a common exon of the tat and rev genes which are used in alternate reading frames. Genes encoding these Rz were cloned into the LTR-neo (LN) retroviral vector under the transcriptional control of two different RNA polymerase II and one RNA polymerase III promoters. The vectors were packaged as amphitropic virions and used to introduce the Rz into human T-lymphocytes. Expression of vector-derived transcripts containing the Rz in the human T-lymphocytes were examined by Northern gel analyses. The most effective Rz expression was derived from the MoMuLV LTR, which resulted in long, multifunctional, viral length transcripts. Cells transduced with these LTR driven Rz vector constructs were subsequently challenged by inoculations with HIV-1. The T-lymphocytes which expressed catalytically active Rz displayed resistance to HIV-1 replication, whereas cells transduced by catalytically inactive versions of the Rz were not resistant.

Methods. For in vitro RZ assays, each of the Rz was cloned into the NotI-SalI sites of the pBluescript vector SK(+) (Stratagene). Rz RNAs were prepared by transcription of SalI-linearized templates. The HIV substrates were prepared from a cloned SalI-SspI fragment of HIVHXB2 DNA cloned in pBluescript (+). The substrates S$_1$ and S$_2$ were transcribed from DdeI or AvaII digested templates, respectively.

Figure 1A:
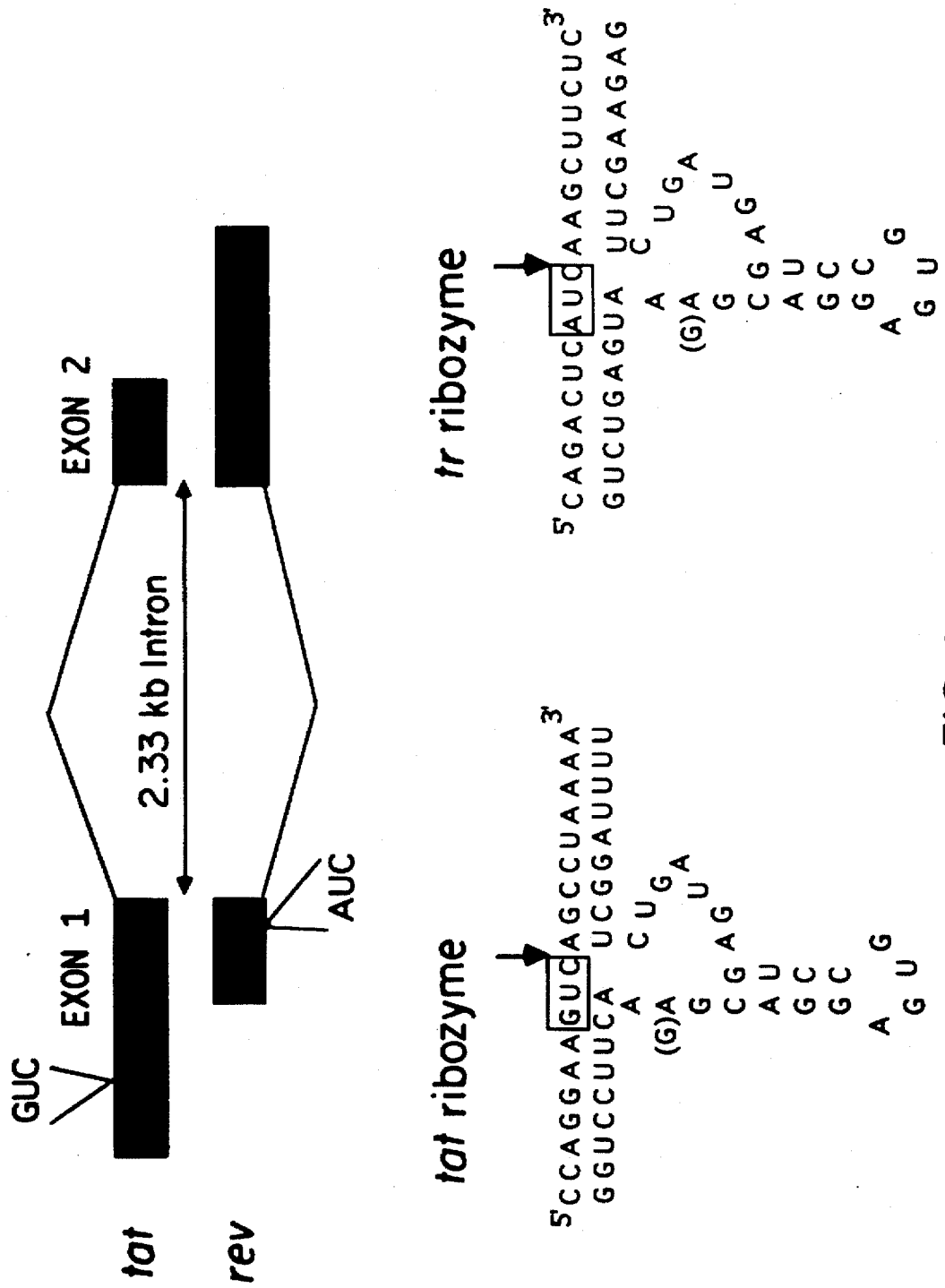
In FIG. 1A, the Rz were designed to contain the consensus core hammerhead Rz catalytic domain flanked by targeting sequences complementary to portions of the HXB2 molecular clone of the HIV-1 genome (Hahn, et al., 1984 (12)). Sequences and locations of the targeting sites of the anti-tat and tat-rev Rz in the HIV-1 genome are nt 5878 and 6025, respectively, in the HIV IIIB isolate. These are schematically depicted as are the Rz base pairing to their respective target RNAs. The (G) represents the position of the nt change in the catalytically inactive mutant Rz. Sites of RZ-mediated cleavage in the target sequences are indicated with arrows.
Figure 1B:
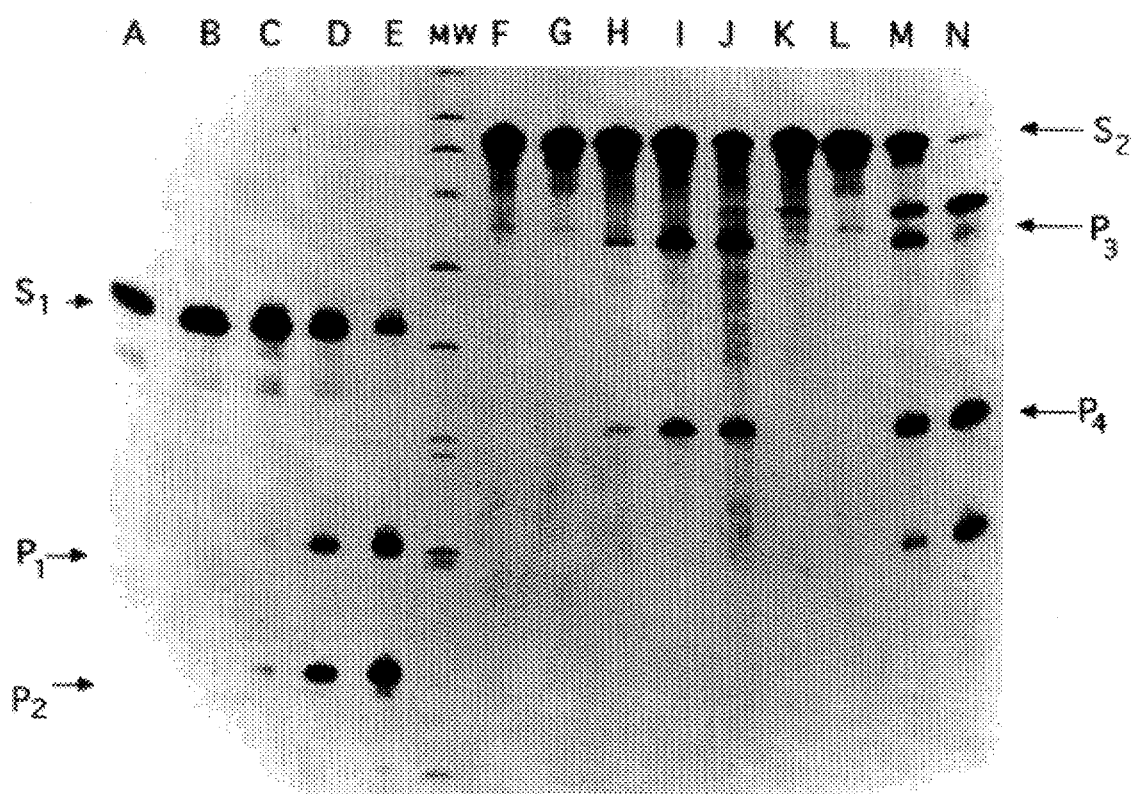
FIG. 1B depicts cleavage of tat and tat-rev RNAs in vitro. Equimolar mixtures of target RNAs and Rz were incubated at the specified temperature for two hours. Lanes A, F, without Rz; lanes A, B, F, G without 20 mM MgCl$_2$; lanes A through C, F, G, H, K, L., the cleavage reaction was at 37° C.; lanes D, I, M, the cleavage reaction was at 45° C.; lanes E, J, N, the cleavage reaction was at 55° C. P$_1$ (117 nt) and P$_2$ (78 nt) are cleavage products of the S$_1$ (195 nt) target of the TAT Rz, and P$_3$ (265 nt) and P$_4$ (152 nt) are cleavage products from the S$_2$ (195 nt) TR Rz target. In lanes M and N, two new products can be observed, one of which migrates just above P$_3$, while the other co-migrates as a doublet with P$_4$. These represent products produced from the S$_2$ transcript as a consequence of cleavage by both the TAT and TR Rz.
Figure 1C:
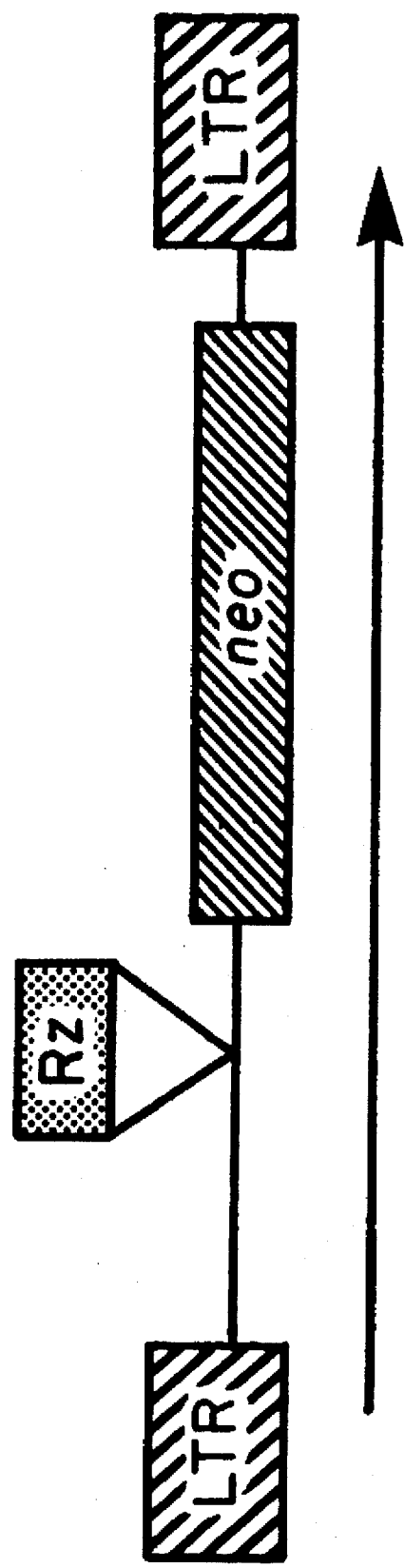
FIG. 1 depicts ribozymes, target sequences and vectors.

FIG. 1C is a schematic representation of the Rz-expressing vectors. The Rz (R) were inserted into the BclI site, 31 bp upstream from the neogene start codon.

Vectors contain the anti-tat Rz (L-TAT-neo), the anti-tat-rev Rz (L-TR-neo), both Rz in tandem (L-TR-TAT-neo) or the two mutant Rz (L-M-TR-TAT-neo) (see section a and panel A). The retroviral vector plasmid pLN was generously provided by A. D. Miller (Fred Hutchinson Cancer Center, Seattle, Wash., USA) and used for construction of all the vectors (Miller and Rosman, 1989 (9)). The orientation and copy number of the Rz in the vectors were confirmed by DNA sequencing.

Methods. PA317 amphitropic packaging cells (also provided by A. D. Miller) were grown in Dulbucceo's minimal essential media (DMEM), high glucose with 10% fetal calf serum (FCS) (Miller and Buttimore, 1986 (13)). Human T-lymphocytes of the CEM cell line were obtained from the American Type Culture Collection (Rockville, Md., USA) and maintained in RPMI with 10% FCS (R10). Clones of PA317 amphitropic packaging cells producing each retroviral vector at high titer were derived essentially as described with some modifications (Miller, et al., (13, 14). In brief, retroviral vector plasmid DNA was transfected into the PA317 amphitropic packaging cell line using DOTAP transfection reagent (Boehringer-Mannheim, Indianapolis, Ind., USA). The transfected PA317 cells were selected in 0.5 mg G418/ml (Geneticin, Bethesda Research Laboratories, Bethesda, Md., USA). Individual clones were expanded and screened for the production of high titer of vector virus, which was assessed by the transfer of G418 resistance to 3T3 cells. High titer clones were expanded and cryopreserved in multiple aliquots for subsequent T lymphocyte transduction. A pre-established PA317 clone which produced the parental LN vector at high titer was obtained from A. D. Miller. T-lymphocytes were transduced by co-cultivation with the high titer PA317 packaging cell clones. The PA317 vector-producing cells were irradiated (4500 rad) and plated at a density of $2\times10^6$ cells/100-mm dish in R10 medium. The next day, $1\times10^6$ cells were added to each plate and the medium was then supplemented with polybrene (Sigma, St. Louis, Mo., USA) to a final concentration of 8 µg/ml. The T-lymphocytes and PA317 cells were co-cultivated for 60 hours and then the non-adherent T-cells were collected and cultured in R10 with 0.5 mgG418/ml until resistant cell pools were obtained (usually two to three weeks later).

Figure 2:
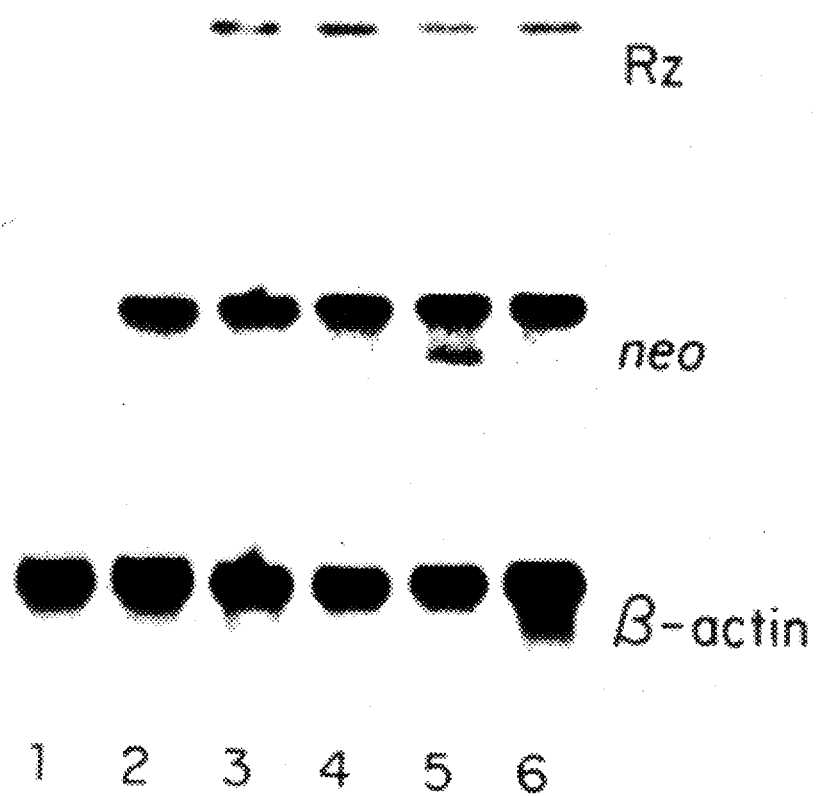

FIG. 2 depicts Northern blot analysis of Rz expression in T-lymphocytes cells. Total cellular RNA was extracted from vector transduced T-cells and analyzed by Northern blot. Total cellular RNA was extracted from the transduced T-cells using the acid-phenol guanidinium thiocyanate method (Chomczynski and Sacchi, 1987 (15)). 20 µg of total cellular RNA were subjected to electrophoresis in a 1% agarose gel containing 5.4% formaldehyde and transferred to nylon membranes. The blots were probed with the Rz genes (as ds DNA removed from the vector plasmids), the neogene from LN, and the human β-actin cDNA (Gunning, et al., 1983 (16)), labeled with [$\alpha$-$^{32}$P]dCTP by the random primer method (Feinberg and Vogelstein, 1984 (17)). RNAs were from non-transduced T-lymphocytes (lane 1), and T-lymphocytes transduced by the LN vector (lane 2), L-TAT-neo (lane 3), L-TR-neo (lane 4), L-TR-tat-neo (lane 5) and L-M-TR-TAT-neo (lane 6). The same blot was successively hybridized with probes consisting of a mixture of the TR and TAT Rz (top row), the neogene (middle row) and the human β-actin cDNA (bottom row).

Figure 3:
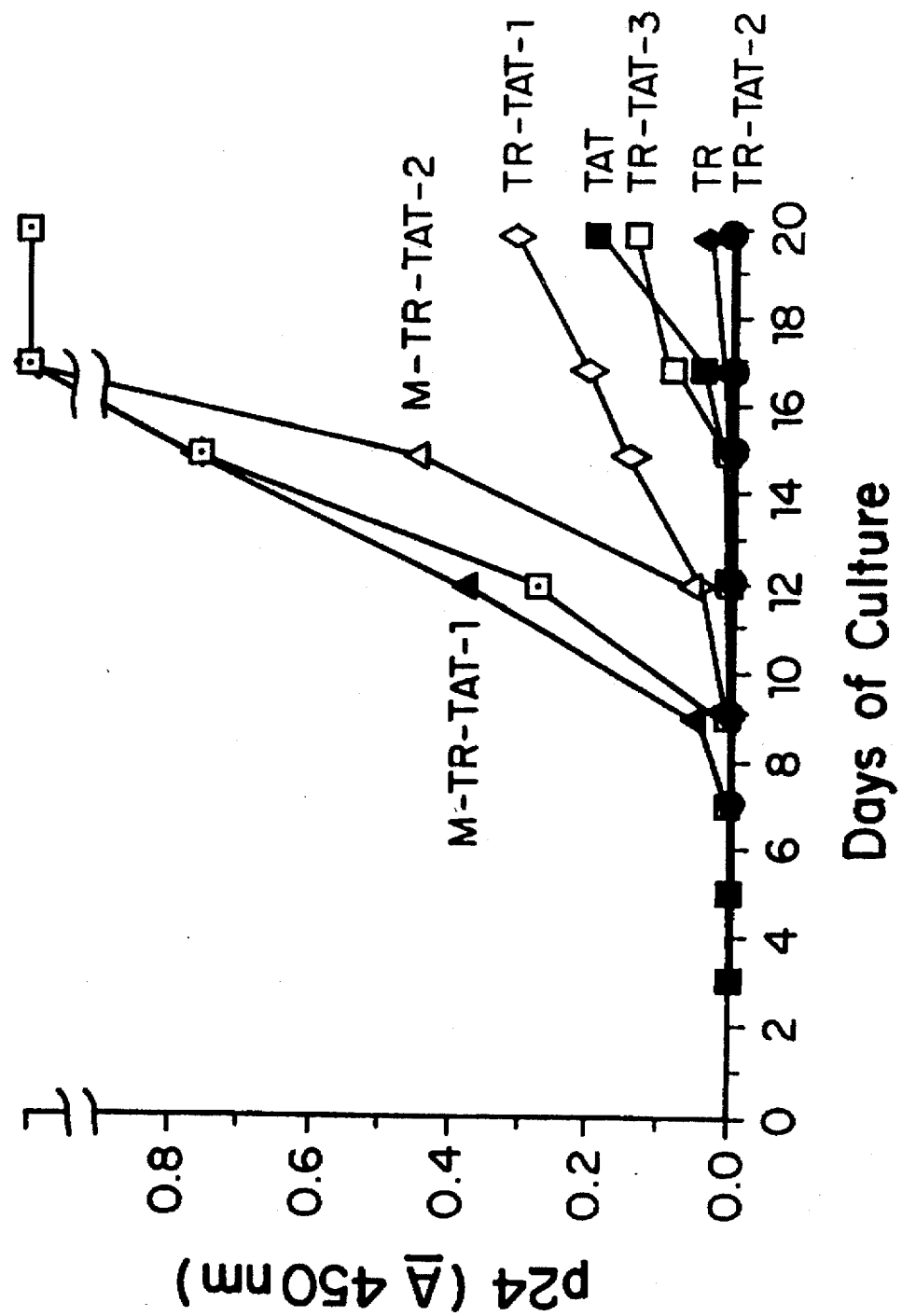

FIG. 3 illustrates that the TAT and TR Rz expressed in T-cells inhibit HIV-1 replication. T-lymphocytes were challenged by infection with HIV-1 on day 0. Samples of culture medium were collected and assayed for p24 gag protein by ELISA at 2–3 day intervals. Cells studied were the parental T-lymphocytes (CEM, dotted squares), T-lymphocytes transduced b the L-TR-neo vector (TR, closed diamonds), T-lymphocytes transduced by the L-TAT-neo vector (TAT, thick squares), three separate pools of T-lymphocytes transduced by the L-TR-TAT-neo vector (TR-TAT-1, 2 and 3, open diamonds, closed squares and open squares), or two separate pools of T-cells transduced by the mutant Rz vector L-M-TR-TAT-neo (M-TR-TAT-1, 2, closed triangles and open triangles).

Methods. HIV-1 of the HTLV-IIIb strain was obtained from the AIDS Research and Reference Reagent Program as a cell free concentrated virus stock at $2.91\times10^7$ virus particles/ml. All work with HIV-1 was performed under BL2 containment conditions. T-lymphocytes cells which had been transduced by the retroviral vectors and selected in LG418 were assayed for resistance to HIV infection. The transdused dT-lymphocytes cells were allowed to grow for at least one week in the absence of G418, prior to HIV-1 challenge. $1\times10^6$ T-lymphocytes were pre-treated with polybrene (8 µg/ml) in 2 ml of R10 for two hours at 37° C. The cells were then washed with 10 ml of R10 and resuspended in 100 µl of HIV-1 diluted in R10 (total of 150 TCID50 per sample), and incubated for two hours at 37° C. After exposure to HIV-1, the cells were washed once with 10 ml of R10 and $5\times10^5$ cells were plated in 25 ml of R10 in flasks and incubated at 37° C. Aliquots of medium were removed from the cultures at 2–3 day intervals after infection and assayed for HIV replication by measurements of HIV-1 p24 antigen production, using an ELISA assay kit (Coulter, Hialeah, Fla., USA).

GENERAL DESCRIPTION AND EXEMPLIFICATION OF THE INVENTION (a) Design of the Rz and retroviral vectors Rz were designed to cleave sequences within the HIV-1 tat (TAT) gene and a tat/rev common exon (TR), as indicated in FIG. 1A. These sites are highly conserved among all known HIV-1 isolates and present in all of the various unspliced, singly-spliced and multiply-spliced HIV-1 RNA present in infected cells, as well as in the genomic RNA of the virion. Cleavage of the HIV-1 RNA at either of these sites would be expected to prevent translation of HIV-1 mRNA or reverse transcription of the genome. In contrast, Rz targeted against structural genes, such as gag, pol or env, would not interfere with expression of the tat, rev or nef, because the target sequences within the structural genes are absent from the doubly spliced RNAs which encode the regulatory proteins.

To control for antisense effects of the Rz, mutant versions of each Rz, designated as M-TAT and M-TR, which have ant substitution at an essential base of the active site and lack cleavage activity (data not shown), were also synthesized (FIG. 1A). The mutants have similar antisense effects to the Rz, but lack catalytic cleavage activity. Therefore, greater inhibitory activity against HIV-1 produced by the wild-type Rz over that seen with the mutant Rz vectors would imply the importance of the Rz catalytic cleavage activity for the anti-viral effects. The activities of TAT and TR Rz were first assayed utilizing an in vitro cleavage assay against synthetic transcripts which contain the specific HIV-1 target sequences (FIG. 1B). Cleavage by the individual or combined Rz resulted in the appearance of cleavage products of the expected size. The combined Rz had a somewhat synergistic effect resulting in greater than 90% cleavage of the target transcript under these conditions.

(b) Retroviral vectors to transduce the Rz.

The retroviral vector LN was used as a Rz delivery vehicle. The TAT or TR Rz were cloned under the transcriptional control of either the viral MoMLV, the human CMV IE promoter (Bahner eta l., 1993 (18)), or a double copy tRNA$^{Met}$ (DCT) promoter (Sullenger, et al., 1990 (19)). The resultant vectors were stably transduced into the human T-lymphocyte cell line CME. Rz RNA expression from each of these promoters was assayed via Northern gel analyses. The levels of expression from both the CMV and DCT promoters were very weak in comparison to the LTR-driven transcripts (data not shown), and they were therefore excluded from further use in these studies.

Either the individual TAT and TR Rz or a tandem combination of both Rz, or a combination of mutant versions of the two Rz, were cloned into the LN retroviral vector plasmid. Rz were inserted into the BclI site of pLN, 31 bp upstream from the ATG start codon of the neogene (FIG. 1C). These vectors would produce a single primary transcript of approximately 2700 nt in length, from the transcriptional start point in the 5' LTR extending to the polyadenylation signal in the 3' LTR. The vector transcript serves multiple functions including: (i) acting as the viral genome of the amphitropic virion produced by the packaging cell line; (ii) encoding the neomycin phosphotransferase protein; and (iii) containing the Rz sequences. The presence of the 5' MoMuLV splice donor and a cryptic splice acceptor, located upstream from the BclI site into which the Rz were inserted, results in the production of a second, slightly shorter transcript, which would lack the packaging signal, but would also contain the Rz and neo sequences. The Rz produced from this vector would be flanked by approximately 1000 nt 5' and 1700 nt 3' of the Rz in a polyadenylated RNA.

(c) Expression of Rz in T lymphocytes

The Rz retroviral vectors were packaged as amphitropic virions in the PA317 cell line and used to transduce human T-lymphocytes. Following gene transfer, the cells were placed under selection with the Nm analogue G418 to produce pools of cells which contain the vectors. Control cells were produced by transduction with the parental neogene vector, LN, which lacks Rz sequences, followed by selection in G418.

Expression of RNA transcripts by the different vector constructs in the 1T-lymphocytes was analyzed by Northern blot analyses. As expected and illustrated in FIG. 2, the parental T-cells and T-cells transduced by the parental LN vector did not show any RNA which hybridized with the Rz probes (lanes 1 and 2). The full-length vector transcripts from the LTR were seen at the expected size of 2700 nt in the T-lymphocytes transduced by each of the Rz vectors. The levels of the vector-specific transcripts were very similar in each of the cell pools. The singly-spliced vector transcripts were not seen in this exposure, but following a prolonged exposure of the blot (twenty days), faint hybridization bands of the predicted sizes were seen, suggesting that most of the vector transcripts remained unspliced in the T-cells. Re-probing of the blot with the neogene showed the same vector transcripts as seen with the Rz probe and also demonstrated the presence of a similar transcript in the LN transduced cells, which lacked the Rz sequences. Re-probing a third time with a human β-actin cDNA verified that nearly equal amounts of RNA were analyzed from each cell pool (FIG. 2).

(d) Inhibition of HIV-1 replication in T-lymphocytes

To test the ability of the Rz to inhibit HIV-1 replication, the Rz-transduced cells with infectious HIV-1 IIIb were challenged. Samples of the culture supernatant were collected at various times and assayed by ELISA for the presence of HIV-1 p24 antigen. Three separate pools of T-cells transduced by L-TR-TAT-neo (TR-TAT-1, 2 and 3) were prepared and analyzed. Two sets of control cells were used: non-transduced T-lymphocytes and T-lymphocytes transduced with the parental LN vector and subjected to G418 selection.

The results of an HIV-1 challenge experiment are shown in FIG. 3. Control T-cells readily supported HIV-1 replication, with the virus growing-out by twelve days after infection. Compared to control cells, T-cells transduced by either the single Rz L-TAT-neo or L-TR-neo or tandem Rz L-TR-TAT-neo showed resistance to HIV infection, with viral out-growth delayed to at least day 20. Nearly equal levels of inhibition were seen with vectors carrying either the TAT or TR Rz or with the vector containing the two Rz in tandem.

The results of this experiment (experiment 1) and a second separate assay (experiment 2) are summarized in Table I. In the second experiment, HIV-1 out-growth from the control cells occurred by day 9. The cells transduced by the Rz vectors again showed inhibition of HIV-1 growth, with virus production delayed until days 12–15.

TABLE I

Effects of ribozymes on HIV-1 replication in T-lymphocytes

| Vector | Day of HIV-1 out-growth* | |
|---|---|---|
| | Experiment 1 | Experiment 2 |
| None | 12 | 9 |
| LN | n.d. | 9 |
| L-TAT-neo | 20 | 15 |
| L-TR-neo | >20 | 12 |
| L-TR-TAT-neo | | |
| Pool 1 | 20 | 15 |
| Pool 2 | >20 | 15 |
| Pool 3 | >20 | 15 |
| L-M-TR-TAT-neo | | |
| Pool 1 | 12 | 12 |
| Pool 3 | 15 | 12 |

*Out-growth was determined by an ELISA measurement of p24 protein levels exceeding an $A_{420nm}$ of 0.20. n.d., not done.

As a control for inhibition of HIV-1 due to antisense effects of the sequences flanking the catalytic domain which are complementary to HIV-1, a vector was made containing mutant versions of the TR/TAT Rz dimer. The mutants contain substitutions of one base within each of the key catalytic hammerhead regions, which has been observed to completely eliminate in vitro cleavage activity. The T-lymphocytes cells with the mutant tandem Rz (L-M-1TR-1TAT-neo) showed little or no inhibition of HIV-1 replications. These findings are consistent with the essential role of the catalytic Rz domain in cleaving viral RNA to produce inhibition of HIV-1 growth.

(e) Conclusions

1. Regulatory gene encoding transcripts as Rz or antisense targets

The earliest RNA transcripts from HIV-1 which appear in the cytoplasm are doubly spliced and encode the regulatory genes tat, rev and nef, these transcripts contain the target sequences for the anti-tat (TAT) and tat-rev (TR) Rz. Thus, inhibition of expression by these Rz would be expected for the genes of the regulatory proteins tat, rev and nef, as well as for those encoding the virion structural and enzymatic proteins. A vector containing both TAT and TR Rz in tandem (L-TR-TAT-neo) was equally inhibitory to the vectors which contained either of the Rz singly (L-TAT-neo or L-TR-neo). Although the tandem Rz vector was not found to be superior to the single Rz vectors in the cell culture assay, there may be in vivo advantages to having multiple Rz against different HIV-1 target sequences in a single vector. Potentially, multimeric Rz targeting different portions of the genome may be less susceptible to the loss of inhibition, due to the development of sequence heterogeneity by HIV-1 at the target site, than would be a single Rz (Chen, et al., 1992 (20)).

The results comparing functional and mutant, inactive Rz document the importance of a functional catalytic Rz core for the inhibition of HIV-1. The results are somewhat in contradiction to those of Lo et al. (1992) (21), who found that a retroviral vector expressing an antisense RNA to a nearby site of the HIV-1 tat gene, but lacking any Rz catalytic domain, was more inhibitory to HIV-1 than was a vector expressing a hammerhead Rz to the same site as the one which was targeted.

2. Improving Rz efficacy

The vector constructs which were used were relatively simple, containing only a single transcriptional unit from the MoMuLV Ltr. Transcripts containing the Rz were readily detected by Northern blot analysis. It was found that this type of vector produced higher levels of Rz RNA than did vectors in which the Rz was expressed from either an internal CMV promoter or a pair of tRNA$^{Met}$ promoters contained within the vector LTR (C.Z. and D.B.K., data not shown). The steady-state levels of Rz which accumulate in cells is a function of both the rate of their production as well as degradation. It may be possible to achieve more inhibition of HIV-1 with higher intracellular levels of Rz by using more active transcriptional units or by adding sequences, such as stem loops, which further stabilize the Rz transcripts. In the L-RBZ-neo type vector, the Rz are contained within long viral transcripts of almost 3000 nt. The ability of the Rz to have significant cleavage activity which inhibits HIV-1 replication in the context of such long transcripts was somewhat surprising. One possible explanation for this observed functional activity in this unlikely RNA context is that the HIV-1 and Rz transcripts are co-localizing to the same intracellular sites. This may be a consequence of the relative lack of splicing of the Rz transcripts, forcing them into the same cellular pathway as the HIV-1 full-length, unspliced viral transcripts. Co-localization of Rz and target RNAs for retroviral encoded transcripts has been demonstrated by Sullenger and Cech (1993) (22), although in their example both transcripts shared the same MoMuLV packaging signals. Efficacy with the long viral transcripts needs to be further examined to determine whether or not this is a function of intracellular co-localization.

3. Rz as inhibitors of HIV replication

Sarver et al. (1993) (23) first reported intracellular cleavage of HIV-1 RNA by a Rz. In their study, a hammerhead Rz directed against the 5' part of the gag gene expressed from a plasmid with the human β-actin promoter was introduced by transfection into CD4+HeLa cells. The cells transduced by the Rz showed decreased levels of HIV-1 RNA and p24 release after infection by HIV-1. Weerasinghe, et al., (1991) (24) produced a hammerhead Rz directed against the 5' leader region of HIV-1 in a variety of retroviral vector constructs and transduced the MT$_4$ human T-cell line. HIV-1 replication was inhibited most effectively when the Rz was expressed under control of a fusion promoter consisting of the Herpes simplex thymidine kinase promoter and the HIV-1 TAR element. Dropulic et al., (1992) (25) demonstrated that a hammerhead Rz directed against the U5 region of the HIV-1 genome, expressed under transcriptional control of the MoMuLV LTR of a retroviral vector, inhibited HIV-1 replication in chronically infected H9 T-lymphocytes and MT$_4$ cells. Chen, et al., (1992) (20) produced a multimeric complex of nine Rz directed against different targets of the HIV-1 env region which inhibited HIV-1 in a transient transfection assay. Yu, et al. (1993) (26) have reported that a hairpin Rz directed against the 5' leader region of HIV-1 inhibited HIV-1 expressed by transient transfection assays in HeLa cells. The use of this hairpin Rz has recently been approved by the NIH DNA Recombinant Advisory Committee for a clinical trial for transduction of patients' peripheral blood T-lymphocytes. Thus, a variety of Rz expression vectors have shown promise as anti-HIV-1 agents.

4. Potential advantages of Rz as anti-viral therapeutic agents

Rz would be expected to lack immunogenicity because they do not encode proteins, in contrast to strategies, such as trans-dominant inhibitory mutants, which rely on the production of foreign proteins. The specificity for inhibiting complementary sequences of nucleic acids may minimize interference with normal cellular functions. RNA decoys which compete for either the TAT or REV proteins may also sequester normal cellular proteins which bind to the RNA domains directly or through binding to the HIV-1 proteins. Additional studies to identify optimal transcriptional control elements to maximize Rz production with the optimal intracellular localization must also be performed. Finally, clinical trials will be needed to assess whether peripheral blood T-lymphocytes or bone marrow stem cells afford better targets for Rz gene therapy of AIDS.

BIBLIOGRAPHY

1. Baltimore, D., *Nature* 335: 395–396 (1988)
2. Szbalski, W., *BioEssays* 14: 495–500 (1992)
3. Sarver, N., et al., *J.NIH Res.* 5:63–67 (1993)
4. Zaug, A. J., et al., *Science* 231: 470–475 (1986)
5. Uhlenbeck, O. C. *Nature* 328: 596–600 (1987)
6. Castanotto, D., et al., *Crit. Rev. Euk. Gene Exp.* 2: 331–357 (1992)
7. Mulligan, R. C., *Science* 260: 926–932 (1993)
8. Williams, D. A., *Hum. Gene Ther.* 1: 229–239 (1990)
9. Miller, A. D., *Biotechniques* 7: 980–990 (1989)
10. Miller, A. D., *Hum. Gene Ther.* 1: 5–14 (1990)
11. Anderson, W. F., et al., *Hum. Gene Ther.* 4: 311–321 (1993)
12. Hahn, B. H., et al., *Nature* 312: 166–169 (1984)
13. Miller, A. D., et al., *Mol. Cell. Biol.* 6: 2895–2902 (1986)
14. Miller, A. D., et al., *Cell Mol. Genet.* 12: 175–183 (1986)
15. Chomczynski, P., et al., *Anal. Biochem.* 162: 156–159 (1987)
16. Gunning, P., et al., *Mol. Cell. Biol.* 3: 787–795 (1983)
17. Feinberg, A. P., et al., *Anal. Biochem* 137: 266 (1984)
18. Bahner, I., et al., *J. Virol.* 67: 3199–3207 (1993)
19. Sullenger, B. A., et al., *Mol. Cell. Biol.* 10: 6512–6523 (1990)
20. Chen, C. J., et al., *Nucleic Acids Res.* 20: 4581–4589 (1992)
21. Lo, K., et al., *Virology* 190: 176–183 (1992)
22. Sullenger, B. A., et al., *Science* 262: 1566–1569 (1993)
23. Sarver, N., et al., *J. NIH Res.* 5: 63–67 (1993)
24. Weerasinghe, M., et al., *J. Virol.* 65: 5531–5534 (1991)
25. Dropulic, B., et al., *J. Virol.* 66: 1432–1441 (1992)
26. Yu, M., et al., *Proc. Natl. Acad. Sci. USA* 90: 6340–6344 (1993)

I claim:

1. The tat ribozyme set forth in SEQ ID NO 2.
2. The vector L-TAT-neo.
3. The vector L-TR-neo.
4. The tr ribozyme set forth in SEQ. ID NO 4.
5. A vector containing the tat ribozyme of SEQ ID NO 2 or the tr ribozyme of SEQ ID NO 4 or both the tat ribozyme of SEQ ID NO 2 and the tr ribozyme of SEQ ID NO 4.
6. The vector L-TR-TAT-neo.
7. A human T-lymphocyte transduced in vitro with a vector of claim 6.
8. An HIV-1 infected mammalian cell transduced in vitro with a vector of claim 6.
9. A method which comprises:
 (i) providing a mammalian cell infected with HIV-1, and
 (ii) transducing said cell in vitro with a vector of claim 6 wherein replication of HIV-1 by said cell infected with HIV-1 is inhibited.
10. A human T-lymphocyte transduced in vitro with a vector of claim 7, claim 2 or claim 3.
11. A method which comprises:
 (i) providing a mammalian cell infected with HIV-1, and
 (ii) transducing said cell in vitro with a vector of claim 7, claim 2 or claim 3
wherein replication of HIV-1 by said cell infected with HIV-1 is inhibited.

* * * * *

UNITED STATES PATENT AND TRADEMARK OFFICE
CERTIFICATE OF CORRECTION

PATENT NO. : 5,695,938
DATED : December 9, 1997
INVENTOR(S) : John J. Rossi

It is certified that error appears in the above-indentified patent and that said Letters Patent is hereby corrected as shown below:

Col. 2, line 67, "neogene" should be -- neo gene --; Col. 3, line 54, "neogene" should be -- neo gene --; same Col., line 62, "neogene" should be -- neo gene --; Col. 4, line 52, "ant" should be -- a nt --; Col. 5, line 18, "neogene" should be -- neo gene --; same Col., lines 40-41, "neogene" should be -- neo gene --;
In the Claims: Col. 10, line 58 (claim 10); "claim 7" should be -- claim 5 --; same Col., line 61 (claim 11), "claim 7" should be -- claim 5 --.

Signed and Sealed this

Seventeenth Day of March, 1998

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 19
( B ) TYPE: Nucleotide
( C ) STRANDEDNESS: Single
( D ) TOPOLOGY: Unknown ( i x ) SEQUENCE DESCRIPTION: SEQ ID NO: 1:

CCAGGAAGUC AGCCUAAAA 19

( 2 ) INFORMATION FOR SEQ ID NO: 2:

( i ) SEQUENCE CHARACTERISTICS:
( A ) LENGTH: 41
( B ) TYPE: Nucleotide
( C ) STRANDEDNESS: Single
( D ) TOPOLOGY: Unknown ( i x ) SEQUENCE DESCRIPTION: SEQ ID NO: 2:

GGUCCUUCAA GAGCAGGAGU GCCUGAGUAG UCUCGGAUUU U 41

( 2 ) INFORMATION FOR SEQ ID NO: 3:

( i ) SEQUENCE CHARACTERISTICS:
( A ) LENGTH: 19
( B ) TYPE: Nucleotide
( C ) STRANDEDNESS: Single
( D ) TOPOLOGY: Unknown ( i x ) SEQUENCE DESCRIPTION: SEQ ID NO: 3:

CAGACUCAUC AAGCUUCUC 19

( 2 ) INFORMATION FOR SEQ ID NO: 4:

( i ) SEQUENCE CHARACTERISTICS:
( A ) LENGTH: 41
( B ) TYPE: Nucleotide
( C ) STRANDEDNESS: Single
( D ) TOPOLOGY: Unknown ( i x ) SEQUENCE DESCRIPTION: SEQ ID NO: 4:

GUCUGAGUAA GAGCAGGAGU GCCUGAGUAG UCUUCGAAGA G 41